US010413188B2

(12) United States Patent
Demos (10) Patent No.: US 10,413,188 B2
(45) Date of Patent: Sep. 17, 2019

(54) ASSESSMENT OF TISSUE OR LESION DEPTH USING TEMPORALLY RESOLVED LIGHT SCATTERING SPECTROSCOPY (71) Applicant: Lawrence Livermore National Security, LLC, Livermore, CA (US)

(72) Inventor: Stavros G. Demos, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1413 days.

(21) Appl. No.: 13/796,880

(22) Filed: Mar. 12, 2013

(65) Prior Publication Data

US 2013/0253330 A1 Sep. 26, 2013

Related U.S. Application Data (63) Continuation-in-part of application No. 11/414,009, filed on Apr. 27, 2006, which is a continuation-in-part
(Continued)

(51) Int. Cl.
*A61B 18/00* (2006.01)
*A61B 5/00* (2006.01)
(Continued)

(52) U.S. Cl.
CPC .......... *A61B 5/0075* (2013.01); *A61B 5/0084* (2013.01); *A61B 5/0086* (2013.01);
(Continued)

(58) Field of Classification Search
CPC ... A61B 5/0075; A61B 5/0084; A61B 5/0086; A61B 2090/062; A61B 2017/00061; A61B 2017/00066
See application file for complete search history.

(56) References Cited

U.S. PATENT DOCUMENTS 4,913,142 A  4/1990  Kittrell et al.
5,071,417 A  12/1991  Sinofsky
(Continued)

FOREIGN PATENT DOCUMENTS

EP  0467459 A  1/1992
EP  1065970  10/2008
(Continued)

OTHER PUBLICATIONS

European Office Action for EP2015672 dated Feb. 1, 2013, corresponding to U.S. Appl. No. 11/414,009, 4 pages.
(Continued)

*Primary Examiner* — Jaymi E Della
(74) *Attorney, Agent, or Firm* — John P. Wooldridge (57) ABSTRACT A method is described to enhance the ability to evaluate the depth of a tissue component or a lesion having optical properties different from a surrounding tissue using time resolved optical methods. This invention may be particularly suitable for the evaluation of lesion depth during RF ablation (irreversible tissue modification/damage) using specially designed devises (catheters) that deliver heat in a localized region for therapeutic reasons. The technique allows for increased ability to evaluate the depth of the ablated lesion or detect the presence of other processes such as microbubble formation and coagulation with higher sensitivity compared to that offered by steady state spectroscopy. The method can be used for in-vivo, real-time monitoring during tissue ablation or other procedures where information on the depth of a lesion or tissue is needed. Exemplary uses are found in tissue ablation, tissue thermal damage, lesion and tissue depth assessment in medical applications.

31 Claims, 5 Drawing Sheets

Related U.S. Application Data of application No. 11/281,853, filed on Nov. 17, 2005, now abandoned.

(60) Provisional application No. 60/629,166, filed on Nov. 17, 2004.

(51) Int. Cl.

| | | |
|---|---|---|
| *A61B 18/14* | (2006.01) | |
| *A61B 18/22* | (2006.01) | |
| *A61B 18/24* | (2006.01) | |
| *A61B 17/00* | (2006.01) | |
| *A61B 18/08* | (2006.01) | |
| *A61B 18/02* | (2006.01) | |
| *A61B 90/00* | (2016.01) | |

(52) U.S. Cl.
CPC .......... *A61B 18/1492* (2013.01); *A61B 18/22* (2013.01); *A61B 18/24* (2013.01); *A61B 18/082* (2013.01); *A61B 2017/00061* (2013.01); *A61B 2017/00066* (2013.01); *A61B 2018/00351* (2013.01); *A61B 2018/00357* (2013.01); *A61B 2018/0212* (2013.01); *A61B 2090/062* (2016.02)

(56) References Cited

U.S. PATENT DOCUMENTS

| | | | |
|---|---|---|---|
| 5,242,441 A * | 9/1993 | Avitall | A61B 18/1492 600/374 |
| 5,280,788 A | 1/1994 | Janes et al. | |
| 5,304,173 A | 4/1994 | Kittrell et al. | |
| 5,419,323 A | 5/1995 | Kittrell et al. | |
| 5,514,131 A | 5/1996 | Edwards et al. | |
| 5,657,760 A | 8/1997 | Ying et al. | |
| 5,762,609 A | 6/1998 | Benaron et al. | |
| 5,800,350 A | 9/1998 | Coppleson et al. | |
| 5,827,277 A | 10/1998 | Edwards | |
| 6,004,269 A | 12/1999 | Crowley et al. | |
| 6,016,452 A | 1/2000 | Kasevich | |
| 6,047,216 A | 4/2000 | Carl et al. | |
| 6,174,291 B1 * | 1/2001 | McMahon | A61B 5/0071 600/564 |
| 6,522,930 B1 | 2/2003 | Schaer et al. | |
| 7,160,296 B2 | 1/2007 | Pearson et al. | |
| 7,662,152 B2 | 2/2010 | Sharareh et al. | |
| 7,976,537 B2 | 7/2011 | Lieber et al. | |
| 2002/0026127 A1 * | 2/2002 | Balbierz | A61B 18/1206 600/567 |
| 2002/0091381 A1 | 7/2002 | Edwards | |
| 2002/0183729 A1 | 12/2002 | Farr et al. | |
| 2003/0181905 A1 | 9/2003 | Long | |
| 2003/0212394 A1 | 11/2003 | Pearson et al. | |
| 2005/0054937 A1 | 3/2005 | Takaoka et al. | |
| 2005/0171437 A1 | 8/2005 | Carberry | |
| 2006/0122587 A1 * | 6/2006 | Sharareh | A61B 18/22 606/11 |
| 2006/0229515 A1 | 10/2006 | Sharareh et al. | |
| 2007/0287998 A1 * | 12/2007 | Sharareh | A61B 18/1492 606/41 |
| 2009/0005768 A1 * | 1/2009 | Sharareh | A61B 18/1492 606/17 |
| 2010/0286530 A1 * | 11/2010 | Paul | A61B 5/0084 600/478 |

FOREIGN PATENT DOCUMENTS

| | | |
|---|---|---|
| EP | 2015672 | 7/2016 |
| WO | 1993/03672 A | 3/1993 |
| WO | 2001/003599 | 1/2001 |
| WO | 2001/008576 | 2/2001 |
| WO | 2004/016155 A | 2/2004 |
| WO | 2004/028353 | 4/2004 |
| WO | 2006/055733 | 5/2006 |

OTHER PUBLICATIONS

European Search Report for EP2967364 dated Feb. 6, 2017, corresponding to U.S. Appl. No. 13/796,880, 9 pages.

\* cited by examiner

ASSESSMENT OF TISSUE OR LESION DEPTH USING TEMPORALLY RESOLVED LIGHT SCATTERING SPECTROSCOPY

CROSS-REFERENCE TO RELATED APPLICATIONS

This application is a continuation-in-part of U.S. application Ser. No. 11/414,009 titled "Fiber Optic Evaluation of Tissue Modification," filed Apr. 27, 2006, incorporated herein by reference, which is a continuation-in-part of U.S. application Ser. No. 11/281,853, titled "Fiber-Optic Evaluation of Cardiac Tissue Ablation," filed Nov. 17, 2005, incorporated herein by reference, which claims priority to U.S. Provisional Application No. 60/629,166, titled "Fiber-optic Evaluation of Cardiac Tissue Ablation and Optical Spectroscopy," filed on Nov. 17, 2004, incorporated herein by reference.

STATEMENT REGARDING FEDERALLY SPONSORED RESEARCH OR DEVELOPMENT

The United States Government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND OF THE INVENTION

Field of the Invention

The present invention relates to a medical diagnostic. More particularly, the present invention relates to optical interrogation configurations for investigating tissue modification in real-time during medical procedures.

Description of Related Art

The presence of a lesion in a field of normal tissue can often be detected by the changes in the way light interacts with the different tissue components. For example, the visual assessment of a surgeon is dominated by the change in the scattering of the light in the visible part of the spectrum by the different tissue components. The light in the near infrared (NIR) part of the spectrum can also detect such differences arising from changes in the structure and biochemical composition of the tissue components. A well recognized property of the NIR light is that it can penetrate deeper into the tissue, on the order of a few cm, mainly due to reduced absorption by blood but also due to reduced scattering. The dependence of the mean penetration depth of the photons as a function of wavelength in different tissue components forms the basis of the U.S. patent application Ser. No. 11/414,009 (the parent case) entitled "Fiber Optic Evaluation of Tissue Modification," incorporated herein by reference and describing the use of NIR spectroscopy for lesion assessment. Specifically, this application provides a novel approach to characterize critical parameters in real time, particularly suitable for application during radio frequency (RF) ablation of cardiac tissue, by incorporating the use of a fiber-optic probe on a typical ablation catheter. RF ablation is commonly used to treat atrial fibrillation, a heart condition that causes abnormal electrical signals, known as cardiac arrhythmias, to be generated in the endocardial tissue resulting in irregular beating of the heart. The RF energy is delivered locally via ablation electrode catheters that can be inserted percutaneously under local anesthesia into a femoral, brachial, subclavian, or internal jugular vein and positioned in the heart. Current methods have limited effectiveness in measuring lesion formation parameters in real-time or associated adverse conditions.

The parent case enables critical parameters of the process leading to the formation of the lesion to be evaluated in real time including such parameters as catheter-tissue proximity, lesion formation, depth of penetration of the lesion, cross-sectional area of the lesion in the tissue, formation of char during the ablation, recognition of char from non-charred tissue, formation of coagulum around the ablation site, differentiation of coagulated from non-coagulated blood, differentiation of ablated from healthy tissue, and recognition of microbubble formation in the tissue for prevention of steam pop. These assessments are accomplished by analyzing the spectral characteristics of the diffusely reflected light from the tip of the ablation catheter via the incorporation of fibers to deliver the illumination and collect the backscattered light.

The most frequent cause of cardiac arrhythmias is an abnormal routing of electrical signals generated in the endocardial tissue near the atrial or ventricular walls. Catheter ablation can be used to treat cases when arrhythmia cannot be controlled with medication, or in patients that cannot tolerate these medications. Using an ablation catheter or similar probe having an energy-emitting element, usually in the form of radiofrequency (RF) energy, a sufficient amount of energy is delivered in the location of suspected centers of this electrical misfiring, leading to the formation of a lesion. These lesions are intended to stop the irregular beating of the heart by creating non-conductive barriers between regions of abnormal electrical activity. Successful treatment depends on the location of the ablation within the heart as well as the spatial characteristics of the lesion.

Attaining contact of the catheter with the tissue is critical for the formation of the lesion. Various methods have been explored as means to provide confirmation of establishing a proper contact during surgery. These means include monitoring of the electrical impedance between the catheter electrode and the dispersive electrode (which utilizes the difference in resistivity between blood and endocardium) along with monitoring the temperature at the tip of the catheter. However, in current practice, these methods do not provide a reliable tool to determine proper contact of the catheter with the tissue. As a result, experience and skill of the electrophysiologist performing the procedure play a major part on the clinical outcome.

The effectiveness of lesion therapy is evaluated by a post ablation monitoring of the electrical signals produced in the heart. If it is determined that signals responsible for arrhythmia are still present (suggesting that the lesion was not adequately formed), additional lesions can be created to form a line of lesions to block passage of abnormal currents. However, there is currently no method to assess in real time how the lesion is forming. The ablation process can also cause undesirable side-effects such as charring of the tissue, localized blood coagulation, and vaporization of tissue water that can lead to steam pocket formation and subsequent implosion (steam pop) that can cause severe complications. All these side effects can be mitigated by adjusting the RF power of the catheter if the operator is aware of their development. Clearly, being limited to post ablation evaluation is undesirable since correction requires additional medical procedures while the surgeon has minimal knowledge regarding the development of undesirable ablation side effects. Thus, there is a need for the development of a guidance tool that could help evaluate the lesion formation parameters in real time as it is being formed in the tissue.

Thermal coagulation of myocardium leads to significant changes in its optical properties. For the case of myocardium coagulation via RF ablation, Swartling et al. reported that the changes in the optical properties in the near infrared (NIR) spectral region include an increase of the scattering coefficient ($\approx$5% higher), a smaller decrease in the scattering anisotropy factor ($\approx$2% lower) and an increase in the absorption coefficient ($\approx$20% higher). We hypothesized that these changes in the optical properties of the RF ablated cardiac tissue can be used to provide in vivo monitoring of lesion formation parameters. Considering that absorption by blood and myocardium in the NIR spectral region is minimal, we postulated that in vivo monitoring may be based on NIR light scattering spectroscopy. Such a method could be employed through the vascular system, preferably as a fiber-optic attachment to the RF ablation catheter.

The parent case teaches a method for the evaluation of lesion formation via RF (or other type of) ablation in real-time using near infrared (NIR) light scattering spectroscopy. The ablation catheter was modified to incorporate spatially separated light emitting and receiving fibers that may be in contact with the tissue as the lesion is formed at the tip of the catheter. Spectral analysis of the light collected by the receiving fiber allows detection of key parameters such as, contact of the catheter with the tissue, onset of lesion formation, depth of penetration of the lesion and, formation of char or coagulum during the ablation.

SUMMARY OF THE INVENTION

The present invention describes a new optical method that offers enhanced capabilities to detect the depth of a lesion. These depths are attained with higher accuracy and increased detection limit. More specifically, as shown in the results provided in the parent case, the ability to detect the depth of the lesion is limited to about 5 mm while there is a distribution of the values that can be considered to be noise. The mechanism that governs the depth detection limit and, in part, the noise is the inherent shortcoming of the prior technique, which uses the spectral information and converts it into depth information. As the intensity of the light that reaches a specific depth is reduced nearly exponentially with depth, the signal detected from different depths is reduced even faster. Thus, most of the signal detected arises from the top layer of the tissue (1-2 mm). Consequently, as the depth of the lesion increases, the signal detected continuously decreases, limiting the ability to characterize the depth of lesions deeper than about 5-8 mm and also contributing to the observed "noise" in the data. To address this problem, the current invention employs a new method that complements the analysis of the spectral information for depth assessment with temporal information by using a pulsed illumination source (or synchronized laser sources) that produces ultrashort pulses of light with sufficiently broad spectrum or pulses of light that cover specific spectral domains over a sufficiently broad spectral range.

To appreciate this concept, one needs to consider the speed of light propagation into the tissue. Given that the index of refraction of tissue is approximately 1.4, photons that are injected at t=0 need at least 45 ps for the round trip to reach the bottom of a 5 mm lesion and then be back-reflected to reach the detector (collection fibers), assuming only ballistic propagation with no multiple scattering. Thus, if the objective of a measurement is to retrieve depth information of a feature located 5 mm below that surface (such as the interface between the normal and ablated cardiac tissue), all signal arriving earlier than about 45 ps contain no useful information.

The change of the scattering properties of the tissue as it transitions from normal to an ablation lesion affects the way light propagates therein and consequently, the temporal profile of the received signal. This would lead to a continuous change of the temporal profile of the received signal starting from the onset of the formation of the lesion. This invention uses this process to generate quantification parameters of the change of the temporal profile that are directly related to the dimensions and other formation parameters of the ablation lesion.

The detection of a tissue component or other features located inside the tissue is based on the existence of wavelength-dependent changes in the optical properties in the NIR spectrum. Determining the depth on a lesion created by RF ablation is one important potential application. This application teaches techniques for detecting other features that relate to the processes involved during RF ablation (or other types of ablation, e.g., the application of heat or cryogenic temperatures), including e.g., the detection of micro-bubbles arising from the heating of the issue. Their detection will be based on the changes in the photon paths due to the large difference in index of refraction between the tissue and the steam located inside the micro-bubbles which will be captured as a change in the temporal profile of the received signal.

Creation of such micro-bubbles has been postulated in the literature and can lead to the formation of steam pops. This is an undesirable process during an ablation procedure. Other applications of this invention include the assessment of tissue depth (such as compartments).

Embodiments of the time resolved approach described herein use pulsed or intensity modulated illumination and time resolved detection schemes. There are multiple ways that such time resolved measurement can be performed and can be found in the scientific literature. For this reason, the exact scheme for the implementation of this aspect of the invention will not be described here. However it may be beneficial for such instrumentation to have the capability to perform both steady state and time resolved measurement so that the benefits described in the prior invention and the invention described in this document can be integrated into a single system.

Recent advances in laser and light sources have provided multiple methods to produce short pulses with broad spectrum via generation of a super-continuum by photonic fibers or other nonlinear materials. Also, compact ultrashort laser sources operating at different wavelengths are available and their cost is rapidly decreasing. In addition, detectors with fast response time are widely available by multiple manufacturers. Therefore, the cost to implement this invention is currently reasonable and is expected to decrease in the future.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

The present invention teaches a different method to assess the lesion spatial parameters in real time with higher precision, especially of deeper ablation lesions. The present method can use the same catheter designs as in the parent case, incorporating optical elements in the tip of the catheter (most commonly in the form of one or more emitting and one or more receiving optical fibers). A schematic of the ablation catheter incorporating optical fibers in an arrangement that is suitable for the current invention is shown in FIGS. 2(a) and 2(b) of the parent case. The present method can also use the ejection of light into the tissue as in the parent case, e.g.; however, while the parent application teaches a method that uses the spectral profile of the receive light in order to assess the lesion depth, the present invention uses the temporal profile of the received light pulse in order to assess the lesion depth.

Figure 1A:
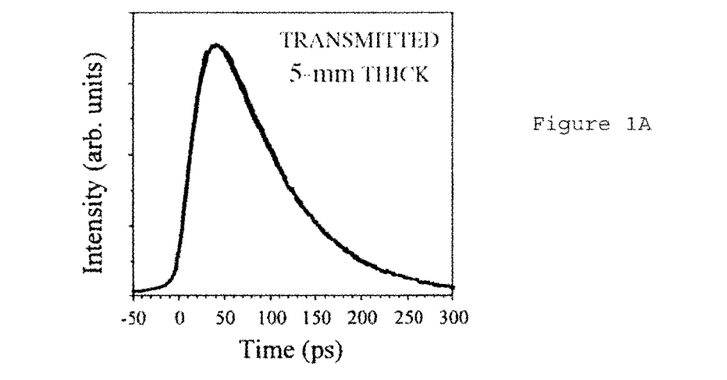
FIGS. 1A-1C show experimental measurements that represent three different temporal profiles of a light pulse emerging from tissue specimens.
Figure 1B:
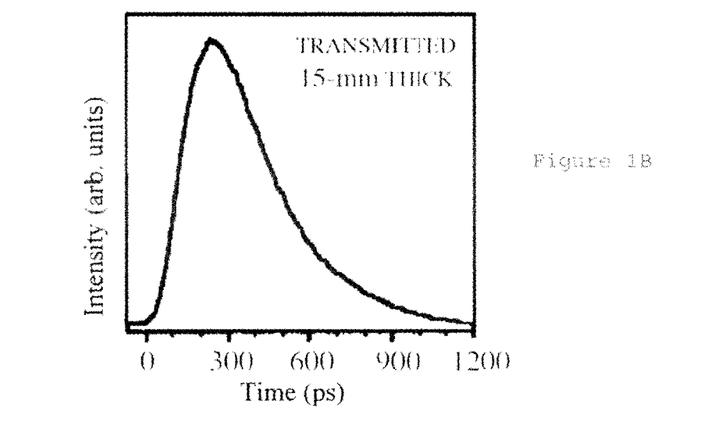
Figure 1C:
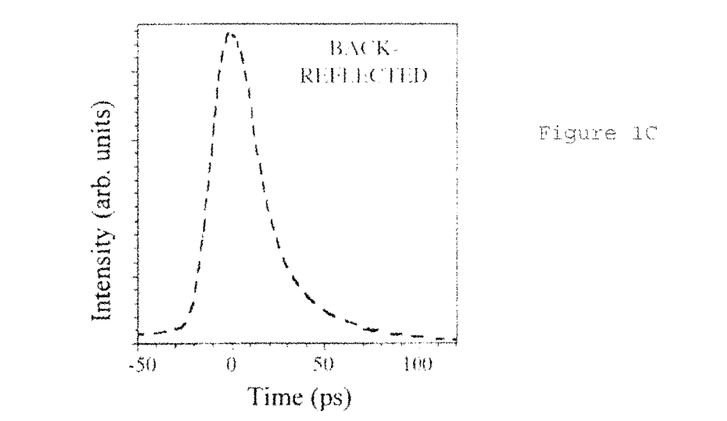

FIGS. 1A-1C show experimental measurements that represent three different temporal profiles of a light pulse emerging from tissue specimens. In all cases, the detected light pulse was the result following the injection of a single light pulse at 1064 nm with temporal duration of about 6.5 ps at full width at half maximum (FWHM). Specifically, the profile shown in FIG. 1A represents the temporal profile of the transmitted light pulse through a 5 mm thick tissue specimen. It can be appreciated that the temporal profile of the emerging light pulse is much broader than the original pulse with the peak positioned at about 50 ps delay but still a significant amount of light is emerging at delays longer than 300 ps. FIG. 1B shows the temporal profile of the transmitted light pulse through a 15 mm thick tissue specimen. The temporal profile of the transmitted pulse is even longer in this case exhibiting a peak at about 300 ps delay while a significant amount of light is still emerging at delays longer than 1000 ps. The above example demonstrates that when a light pulse is injected into the tissue, the transmitted light pulse is delayed and broadened in time as it propagates through the tissue. FIG. 1C shows the temporal profiles of the back-reflected light following injection of a light pulse. It can be appreciated that most of the light is reflected at times shorter than about 50 ps. It is well known that some photons can reach a depth on the order of 5 to 10 mm before they emerge in the backscattering direction. However, this group of photons will arrive at much longer delays, on the order of a few hundreds of ps. These photons that can reach deeper into the tissue can carry information about the tissue structure that is located deeper into the tissue (such as deeper lesions) while the photons arriving earlier can carry information only about the structures closer to the surface of the tissue. With proper use of the underlying mechanism controlling the propagation of light in tissues, this invention teaches a method that uses the temporal characteristics of the emerging light pulse to enhance information regarding lesion depth in real time during tissue modification (such as RF tissue ablation).

Figure 2A:
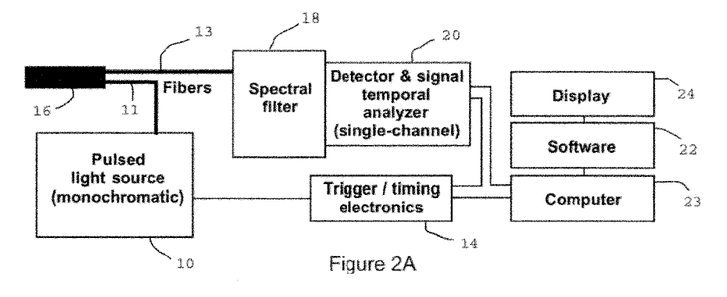
FIG. 2A shows the main components of a fiber optic evaluation system of the present invention when the light source is monochromatic.
Figure 2B:
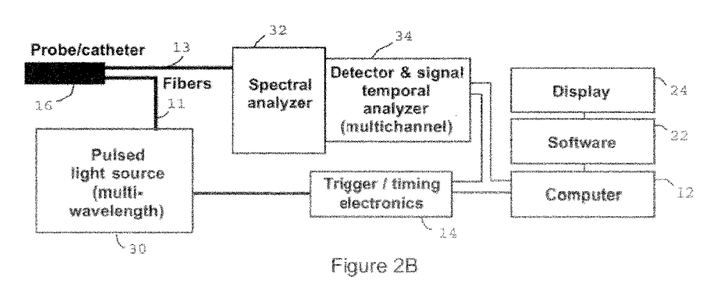
FIG. 2B shows the main components involved when the light source provides illumination at two or more wavelengths.
Figure 2C:
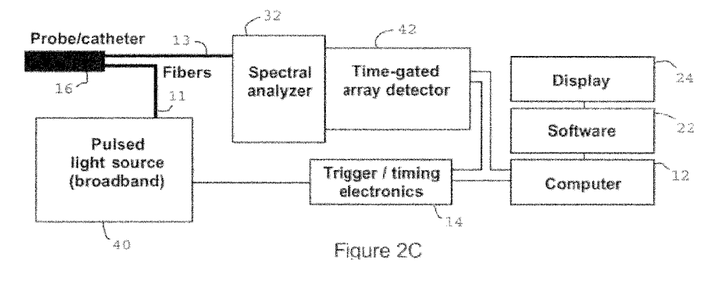
FIG. 2C shows the main components involved when the light source provides a broadband illumination over a relatively wide spectral range.

Simplified diagrams of fiber optic evaluation systems of the present invention are shown in FIGS. 2A-C. Specifically, FIG. 2A shows the main components involved when the light source 10 is monochromatic. In this case, a computer 12 controls the light source pulse trigger/timing electronics 14, so that the monochromatic pulses (optical interrogation radiation) from light source 10 are directed by fiber optic(s) 11 through the probe and ablation catheter 16 to the tissue site simultaneously with the ablation energy. As discussed, herein, a reference signal can be obtained from the tissue site prior to the step of simultaneously ablating the tissue and propagating the interrogation pulse. Other techniques for obtaining the reference signal are discussed herein. Also discussed herein are steps for comparing the radiation induced by the interrogation radiation to the reference signal to produce one or more quantification parameters from which a least one instantaneous condition of the in-vivo cardiac tissue can be determined. Induced radiation is collected in figure optic(s) 13. A spectral filter 18 is used to spectrally clean the collected induced radiation. This light is detected by detector and signal temporal analyzer 20 (e.g., a single channel) allowing its temporal profile to be subsequently recorded by software 22. Subsequently, the signal is analyzed and quantification parameters are estimated and the corresponding lesion formation parameters are displayed by display 24. FIG. 2B shows identical components as FIG. 2A except that two or more wavelengths are provided by a light source 30. In this case, a spectral analyzer 32 is used to spectrally separate the different wavelengths of the detected light by detector and multichannel signal temporal analyzer 34 and their temporal profiles are subsequently recorded and displayed. FIG. 2C shows the main components involved when the light source 40 provides a broadband illumination over a relatively wide spectral range. In this case, the spectral analyzer is used to spectrally separate the different wavelength bands of the light which is detected by a time-gated array detector 42 allowing their temporal profiles to be subsequently recorded and lesion formation parameters are displayed. The systems of FIGS. 2A-2C are exemplary. Other systems will be apparent to those skilled in the art upon understanding the teachings herein.

Figure 3A:
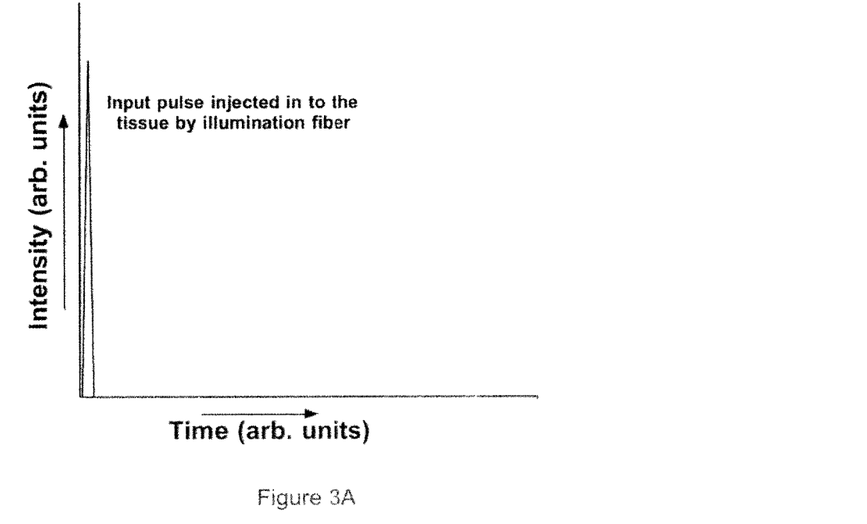
FIG. 3A depicts the temporal profile of the injected light pulse which ideally should be on the order of a few ps or less but it can be as long as on the order of 1 ns.
Figure 3B:
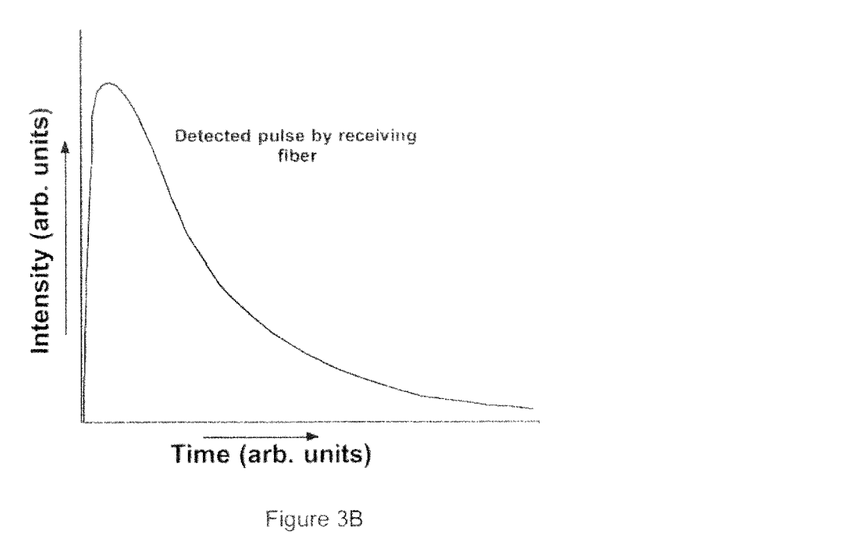
FIG. 3B shows the corresponding temporal profile of the detected light using an arrangement similar to that illustrated in FIG. 1.

FIG. 3A depicts the temporal profile of the injected light pulse, which ideally should be on the order of a few ps or less but it can be as long as on the order of 1 ns. The corresponding temporal profile of the detected light, using an arrangement similar to that illustrated in FIGS. 2(a) and 2(b) of the parent case, is depicted in FIG. 3B. As discussed earlier, the detected light pulse is delayed in time and is broader in duration than the original pulse. Photons reaching larger depths inside the tissue before being collected by the receiving fiber will emerge at longer delays.

Figure 4A:
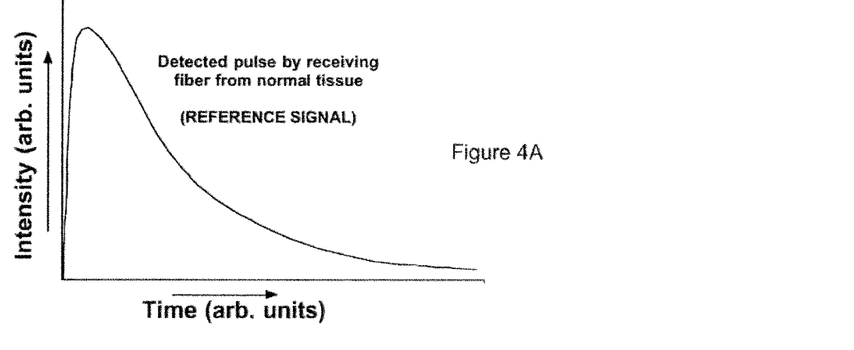
FIG. 4A shows a first temporal profile corresponding to normal tissue when the illumination source is monochromatic.
Figure 4B:
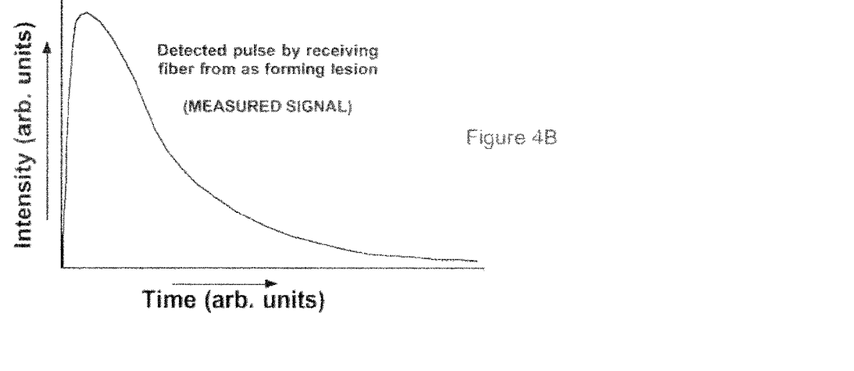
FIG. 4B shows a modification of the detected temporal profile during ablation.
Figure 4C:
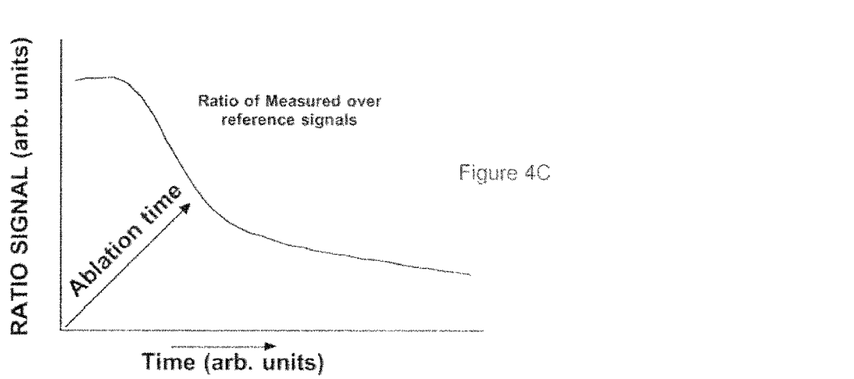
FIG. 4C shows a ratio of the as measured temporal profile divided by the reference profile used for quantification of the change of the tissue modification

Let us now assume the first case when the illumination source is monochromatic. In this case, a first temporal profile corresponding to normal tissue is depicted in FIG. 4A. In a clinical setting, this profile is measured before the onset of ablation and lesion formation or it can be a reference profile representing the signal of normal tissue from the site of tissue ablation. During ablation, the tissue properties will be continuously modified which will result in a modification of the detected temporal profile (depicted in FIG. 4B). This change is directly related to the lesion characteristics. Quantification of this change of the temporal profile will lead to direct information of the lesion parameters. These lesion parameters can be continuously monitored during the tissue ablation procedure. In the example shown in FIG. 4C, a ratio of the as-measured temporal profile divided by the reference profile is used for quantification of the change of the tissue modification (lesion quantification parameter). Other mathematical forms and/or methods can be used to quantify the change of the temporal profile. In the case of the example shown in FIG. 4C, the quantification parameter (QP) is a temporal profile. However, the QP can be a single point along the delay time or multiple points along the delay time forming a set of values. These sets of values can be further utilized to form ratios or other mathematical forms that can quantify the tissue modification (lesion parameters) with a smaller set of values.

Figure 5A:
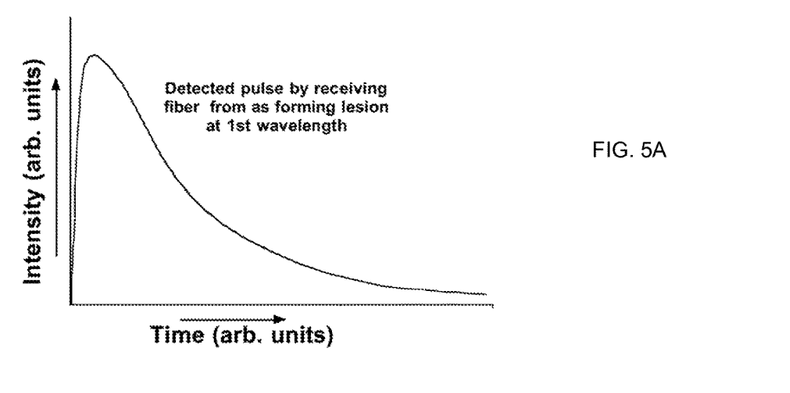
FIGS. 5A and 5B shows that the temporal profiles from each wavelength will differ due to the different scattering and absorption coefficient in the tissue as a function of wavelength.
Figure 5B:
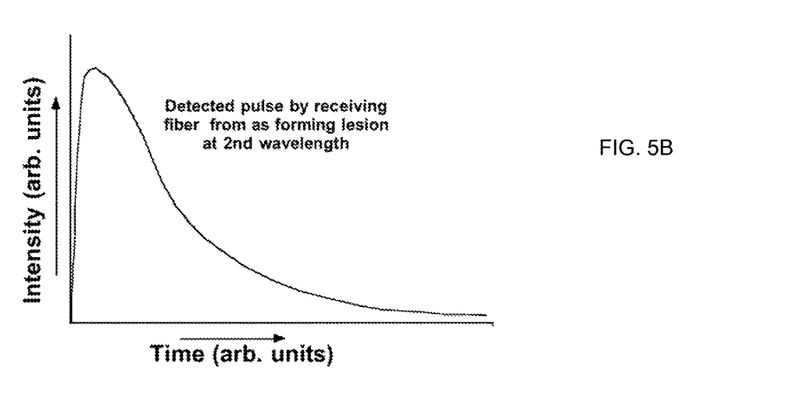
Figure 5C:
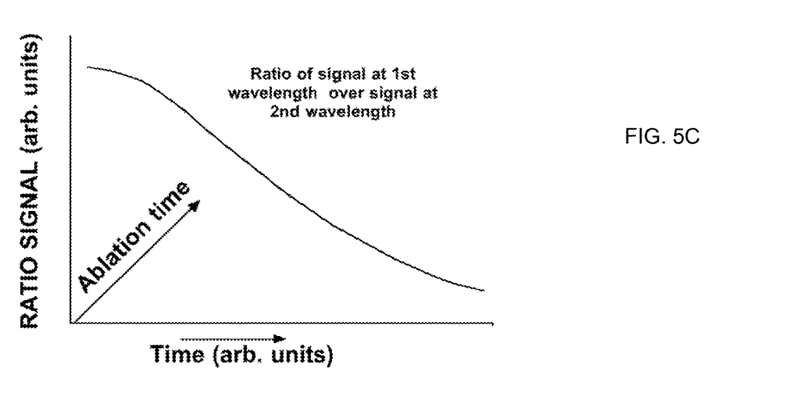
FIG. 5C shows a ratio of the as measured temporal profile at a first wavelength divided by the temporal profile at another wavelength.

Let us now consider the second case when the illumination source provides more than one wavelength. In this case, each wavelength can be treated as in the previous case. In addition, the temporal profiles from each wavelength (depicted in FIGS. 5A and 5B) will differ due to the different scattering and absorption coefficient in the tissue as a function of wavelength. During ablation, the tissue properties will be continuously modified, which will result in a modification of the detected temporal profile recorded at each wavelength. This change is directly related to the lesion characteristics. Quantification of the change of the temporal profile at each wavelength will lead to direct information of the lesion parameters. These parameters can be continuously monitored during the tissue ablation procedure. In the example shown in FIG. 5C, a ratio of the as-measured temporal profile at a first wavelength divided by the temporal profile at another wavelength is used for quantification of the change of the tissue modification (lesion parameter). Other mathematical forms and/or methods can be used to quantify the change of the temporal profile. In the case of the example shown in FIG. 5C, the quantification parameter (QP) is a temporal profile. However, the QP can be a single point along the delay time or multiple points along the delay time forming a set of values. These set of values can be further utilized to form ratios or other mathematical forms that can quantify the tissue modification (lesion parameters) with a smaller set of values.

The same method can be used to analyze the signal when the illumination source provides broadband illumination. In this case, the broadband spectrum is divided in to an appropriate number of smaller spectral regions which thereafter are treated in the same manner as discussed above (see the examples of FIGS. 5A-C).

Lesion assessment in real time can be accomplished by monitoring these predefined quantification parameters (QPs). As mentioned above, these QPs can be different depending on the number of illumination wavelengths. Typically, for the case in which more than one wavelength is used for illumination, each wavelength gives rise to its own detected temporal profile. The method attains additional dimensions because additional QPs can be generated by applying a mathematical formula (such as a ratio) between one or more points along each temporal profile (values of the QP temporal profile at specific delays) or between data points generated from the profiles of different wavelengths for the same time delay or for predetermined delays. In a simple example assuming that only two illumination wavelengths are used, the ratio of the intensity of the detected signal at one or more specific predetermined delays can be used to monitor the formation of the lesion. Other combinations can be used to perform the same task. Reference data for producing quantification parameters can be predetermined and recorded in a database. The reference data correlates to tissue state. Based on the teachings herein, such reference data and QPs can be determined by a variety of methods. Exemplary data useable in such a database are described in the parent application. Other processes for obtaining and using the reference data and the QPs will be apparent to those skilled in the art upon an understanding of the teachings herein.

Accordingly, this disclosure teaches optical time-resolved methods for real-time evaluation of in-vivo cardiac tissue lesion formation parameters. Simultaneously with a step of producing a lesion in in-vivo cardiac tissue, a pulse of optical interrogation radiation is directed onto a first tissue site of the in-vivo cardiac tissue. The induced radiation has at least one signal temporal profile, which is a measure of intensity versus time. By quantifying a difference between signal data derived from the signal temporal profile and reference data from at least one reference temporal profile, at least one quantification parameter (QP) is determined and then at least one instantaneous condition of the in-vivo cardiac tissue is determined from said QP. The catheter described in the parent application can be used to provide ablation energy to the in-vivo cardiac tissue to produce the lesion. In that case, the catheter incorporates at least one optical conduit adapted for directing the pulse of optical interrogation radiation at a first tissue site of the cardiac tissue and includes at least one optical conduit adapted for collecting the induced radiation from a second tissue site of the cardiac tissue. The lesion can be produced by applying RF energy, a cryogenic energy, light energy or heat to the in-vivo cardiac tissue.

Pulses used for interrogation of the in-vivo cardiac tissue may have a variety of pulse durations and formats. Pulse durations may be up to 10 ns in duration but optimally on the order of 10 ps or less. Mono-chromatic light, multiple wavelengths of light or a continuous spectrum of light may be used for the pulsed light. It has been found especially helpful to provide wavelengths within a range from about 600 nm to about 1500 nm. In cases where the pulse consists of multiple wavelengths of light or a continuous spectrum of wavelengths, the signal temporal profile can be separated into a number n of spectral bands, where each spectral band n has a respective temporal profile, which may sometimes be referred to herein as T(n), i.e., the temporal profile of a particular or specific spectral band. Sometimes, it is desirable to detect or separate the signal data into discrete data points for each spectral band n. Thus, a discrete data point on the temporal profile of a specific spectral band may sometimes be referred to in this application as $P\{T(n)\}$. The discrete data points $P\{T(n)\}$ can therefore form a digital representation a particular signal temporal profile of interest, where the digital representation provides signal intensity values at a sequence of specific delay times.

Discrete data points at specific time delays may be normalized in a variety of ways. One way is by dividing at least a portion of the digital representation by a predetermined set of discrete data points. Thus, the QP will include at least one set of normalized discrete data points at specific time delays. Normalization is generally carried out as a function of at least part of a digital representation and a predetermined set of discrete data points. Such predetermined set of discrete data points often may include at least a part of the reference data. Reference temporal profiles may be obtained from the tissue site before the lesion is produced or may be obtained from a pre-existing database. The data within the database can be collected and compiled by a variety of methods which will be understood by those skilled in the art as a result of this disclosure.

It should be noted that the quantification of the difference between signal data derived from the signal temporal profile and reference data from at least one reference temporal profile may be carried out in a variety of ways. This application provides examples of quantification methods. These examples will enable those skilled in the art to understand other methods as well. For example, the quantifying step may comprise applying a mathematic formulation between at least two members of a set of data points P{T(n)} for a plurality of each spectral band n. The step may be accomplished by applying a mathematic formulation between at least two members of a set of data points P{T(n)} for different spectral bands of the each spectral band n. Another way of operating the step is by generating fitting parameters for the set of data points P{T(n)} for the each spectral band n. Still another way of quantifying the difference comprises generating fitting parameters to a data set generated via the application of a mathematical formulation between delay-time-corresponding data points of a set of data points P{T(n)} from different spectral bands of the each spectral band n. Another example for quantifying the difference comprises generating discrete values at one or more specific delay times following the application of a mathematical formulation between data points from different spectral bands at the corresponding specific delay times.

Instantaneous tissue condition may be further used to derive additional information. For example, if the instantaneous condition is determined to be the instantaneous lesion depth at a depth at a particular depth A, since the time to produce the lesion is known, then the rate of formation of the lesion (a rate of cardiac tissue ablation) to that depth A can be determined and the rate of ablation time needed to create a lesion having a greater depth B can be extrapolated. In one useful example, this process determines an instantaneous depth at a depth of about 4 mm, then determines the rate of formation of the lesion to the depth of about 8 mm; and finally extrapolates from the rate the ablation time needed to create a lesion having a depth B that is greater than depth A. In another example, the rate of lesion formation is estimated using a substantially linear relationship between cardiac ablation lesion depth and at least one quantification parameter of the collected radiation for lesion depths up to about 8 mm. In another important example, at least one of the instantaneous lesion depth and the rate of lesion formation are estimated using a monotonic relationship between cardiac ablation lesion depth and at least one quantification parameter of the collected radiation for lesion depths up to about 8 mm. Note that in this and in some other examples, the quantification parameter monotonically changes as lesion depth changes.

This disclosure provides some important examples of ways that the QPs can be interpreted to determine useful information about tissue state. The teachings in this disclosure will enable those skilled in the art to discern other ways of interpreting QPs. For example, the formation of steam microbubles can be detected by monitoring the temporal evolution of one or more of the quantification parameters at different spectral bands as the lesion is produced. By monitoring the change in depth of the lesion per unit time, a rate of tissue ablation can be determined. The presence of coagulum at the lesion can be determined by monitoring the temporal evolution of one or more of the quantification parameters at different spectral bands during the production of the lesion. Also, charring can be detected at the lesion by monitoring the temporal evolution of one or more of the quantification parameters at different spectral bands during the-step of producing a lesion. Further, the rate of change of one or more of the quantification parameters can be used to extrapolate an ablation depth, e.g., of up to about 1.5 cm. The presence of normal tissue, abnormal tissue and proper or non-proper contact of the ablation catheter or other source of energy can be determined by comparing the QP to a normalized reference temporal profile obtained from a pre-existing database.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

I claim:

1. An optical time-resolved method for real-time evaluation of at least one in-vivo cardiac tissue lesion formation parameter, comprising:
   producing a lesion by directing energy through a point on a first surface at a first tissue site in in-vivo cardiac tissue;
   simultaneously with the step of producing said lesion, directing a first single interrogation pulse of optical radiation onto said point on said first surface at said first tissue site to produce a first single return signal pulse of optical radiation induced by scattering of said first single interrogation pulse of optical radiation from said first tissue site, wherein said first single interrogation pulse has a pulse duration up to 10 ns;
   collecting at least a portion of said first single return signal pulse to produce a first single collected radiation pulse having a first signal temporal profile of intensity versus time, wherein said first single return signal pulse is collected only after it propagates from within said lesion and then out of said lesion through said first surface;
   quantifying a first difference between first signal data from said first signal temporal profile of intensity versus time and first reference data from a first reference temporal profile of intensity versus time to produce at least one quantification parameter (QP); and
   determining, from said at least one QP, at least one instantaneous condition of said in-vivo cardiac tissue.

2. The method of claim 1, further comprising providing an ablation catheter configured for delivering said energy to said in-vivo cardiac tissue to produce said lesion and inserting said ablation catheter into said in-vivo cardiac tissue in its vasculature, wherein said ablation catheter further incorporates at least one first optical conduit adapted for directing said first single interrogation pulse of optical radiation at said first tissue site of said in-vivo cardiac tissue and wherein said ablation catheter further incorporates at least one second optical conduit adapted for collecting said first single return signal pulse.

3. The method of claim 1, wherein said lesion is produced by a process selected from the group consisting of (i) applying radiofrequency (RF) energy to said in-vivo cardiac tissue, (ii) applying a cryogenic energy to said in-vivo cardiac tissue (iii) applying light energy to said in-vivo cardiac tissue and (iv) applying heat to said in-vivo cardiac tissue.

4. The method of claim 1, wherein said first single interrogation pulse is selected from the group consisting of mono-chromatic light, multiple wavelengths of light and a continuous spectrum of light.

5. The method of claim 1, wherein said first single interrogation pulse is selected from the group consisting of multiple wavelengths of light and a continuous spectrum of light, the method further comprising separating said first signal temporal profile into a number n of spectral bands, wherein each spectral band n of said spectral bands comprises a respective temporal profile $T(n)$.

6. The method of claim 5, wherein said first signal data comprises at least one set of discrete data points $P\{T(n)\}$ for at least one of said each spectral band.

7. The method of claim 6, wherein one or more of said at least one set of discrete data points $P\{T(n)\}$ forms a digital representation of at least one said respective temporal profile $T(n)$, wherein said digital representation provides signal intensity values at specific delay times across said at least one said respective temporal profile $T(n)$.

8. The method of claim 6, wherein one or more of said at least one set of discrete data points $P\{T(n)\}$ forms at least one digital representation of at least one said respective temporal profile, wherein said at least one digital representation provides signal intensity values at specific delay times, wherein the step of quantifying a first difference comprises dividing at least a portion of said at least one digital representation by said first reference data, wherein said first reference data comprises a predetermined set of discrete data points.

9. The method of claim 6, wherein one or more of said at least one set of discrete data points $P\{T(n)\}$ forms at least one digital representation of at least one said respective temporal profile, wherein said at least one digital representation provides signal intensity values at specific delay times, wherein the step of quantifying a first difference comprises normalizing at least a portion of said at least one digital representation with said first reference data, wherein said first reference date comprises a predetermined set of discrete data points.

10. The method of claim 8, wherein said predetermined set of discrete data points comprises at least a portion of said reference data.

11. The method of claim 1, wherein said first reference temporal profile is obtained from said first tissue site before the step of producing a lesion.

12. The method of claim 1, wherein said first reference temporal profile is obtained from a pre-existing database.

13. The method of claim 8, wherein the step of quantifying the difference comprises applying a mathematic formulation between at least two members of a set of data points $P(n)$ for a plurality of said each spectral band n.

14. The method of claim 8, wherein the step of quantifying the difference comprises applying a mathematic formulation between at least two members of a set of data points $P(n)$ for different spectral bands of said each spectral band n.

15. The method of claim 8, wherein the step of quantifying the difference comprises generating fitting parameters for the said at least one set of discrete data points $P\{T(n)\}$.

16. The method of claim 8, wherein the step of quantifying the difference comprises generating fitting parameters to a data set generated via application of a mathematical formulation between delay-time-corresponding data points of a set of data points $P(n)$ from different spectral bands of said each spectral band n.

17. The method of claim 8, wherein the step of quantifying the difference comprises generating discrete values at one or more of the specific delay times following application of a mathematical formulation between data points from different spectral bands at the one or more of the specific delay times specific delay times.

18. The method of claim 1, wherein said at least one instantaneous condition comprises an instantaneous lesion depth at a depth A, the method further comprising:
   determining a rate of formation of said lesion which is a rate of cardiac tissue ablation to said depth A; and
   extrapolating from said rate of formation of said lesion an ablation time needed to create a lesion having a depth B that is greater than the depth A.

19. The method of claim 1, wherein said at least one instantaneous condition comprises an instantaneous depth at a depth of about 6 mm, the method further comprising:
   determining a rate of formation of said lesion which is a rate of cardiac tissue ablation to said depth of about 6 mm; and
   extrapolating from said rate of formation of said lesion an ablation time needed to create a lesion having a depth of about 8 mm that is greater than the depth of about 6 mm that is greater than depth A.

20. The method of claim 1, wherein said at least one quantification parameter monotonically changes as a depth of said lesion changes.

21. The method of claim 1, further comprising detecting an eruption of at least one steam pop by monitoring temporal evolution of the at least one quantification parameter at different spectral bands during the step of producing the lesion.

22. The method of claim 1, further comprising determining a rate of tissue ablation by monitoring a change in depth of said lesion per unit time.

23. The method of claim 1, further comprising determining whether coagulum exists at said lesion by monitoring temporal evolution of the at least one quantification parameter at different spectral bands during the step of producing the lesion.

24. The method of claim 1, further comprising determining whether charring exists at said lesion by monitoring temporal evolution of the at least one quantification parameter at different spectral bands during the step of producing the lesion.

25. The method of claim 1, wherein said first single interrogation pulse of optical radiation comprises a wavelength within a range from about 600 nm to about 1500 nm.

26. The method of claim 1, wherein said first single interrogation pulse of optical radiation comprises a wavelength within a range from about 600 nm to about 970 nm.

27. The method of claim 1, further comprising extrapolating an ablation depth of up to about 1.5 cm from a rate of change of said at least one quantification parameter (QP).

28. The method of claim 1, further comprising determining, from said at least one quantification parameter, if normal tissue is present, wherein the step of determining if normal tissue is present comprises comparing said at least one QP to a normalized reference temporal profile obtained from a pre-existing database.

29. The method of claim 2, further comprising utilizing one or more changes of said at least one quantification parameter to determine if there is a non-proper contact of said ablation with normal tissue, wherein the step of utilizing comprises comparing said at least one QP to a normalized reference temporal profile obtained from a pre-existing database.

30. The method of claim 1, further comprising determining, from said at least one quantification parameter if abnormal tissue is present, wherein the step of determining if abnormal tissue is present comprises comparing said at least one QP to a normalized reference temporal profile obtained from a pre-existing database.

31. The method of claim 1, further comprising measuring a change of temporal evolution of the at least one quantification parameter at one or more spectral band during the step of producing the lesion, the method further comprising utilizing said change to detect in real time formation of at least one microbubble, wherein said microbubble constitutes a precursor to explosive release of gas or steam pops.

* * * * *